(12) United States Patent
Leyton Virgen et al.

(10) Patent No.: US 9,474,551 B2
(45) Date of Patent: Oct. 25, 2016

(54) EXTERNAL FIXATION DEVICE ADAPTABLE FOR BONE FRACTURES

(75) Inventors: Arlex Leyton Virgen, Cali (CO);
Andres Machado Caicedo, Cali (CO);
Jaime Jose Garcia Alvarez, Cali (CO)

(73) Assignee: UNIVERSIDAD DEL VALLE, Santiago de Cali (CO)

(*) Notice: Subject to any disclaimer, the term of this patent is extended or adjusted under 35 U.S.C. 154(b) by 642 days.

(21) Appl. No.: 13/825,859

(22) PCT Filed: Oct. 9, 2010

(86) PCT No.: PCT/IB2010/054571
§ 371 (c)(1),
(2), (4) Date: May 16, 2013

(87) PCT Pub. No.: WO2012/046109
PCT Pub. Date: Apr. 12, 2012

(65) Prior Publication Data
US 2014/0114310 A1    Apr. 24, 2014

(51) Int. Cl.
*A61B 17/64* (2006.01)
*A61B 17/62* (2006.01)
*A61B 17/66* (2006.01)

(52) U.S. Cl.
CPC ............. *A61B 17/62* (2013.01); *A61B 17/645* (2013.01); *A61B 17/6466* (2013.01); *A61B 17/66* (2013.01)

(58) Field of Classification Search
CPC ................ A61B 17/60; A61B 17/64–17/6491
USPC .................................................... 606/54–59
See application file for complete search history.

(56) References Cited

U.S. PATENT DOCUMENTS

| 4,483,334 | A | * | 11/1984 | Murray | .................. | A61B 17/60 403/391 |
| D314,503 | S | | 2/1991 | Gilman | | |
| 5,863,292 | A | * | 1/1999 | Tosic | ..................... | A61B 17/62 606/56 |
| 6,428,540 | B1 | | 8/2002 | Claes | | |

FOREIGN PATENT DOCUMENTS

| SU | 614790 | 6/1978 |
|---|---|---|
| WO | 9202184 | 2/1992 |
| WO | 9741790 | 11/1997 |
| WO | 9812975 | 2/1998 |
| WO | 02053038 | 7/2002 |

(Continued)

OTHER PUBLICATIONS

Chao, et al., "Comparison of the mechanical performance of three types of external fixators: linear, circular and hybrid." Clinic Biomechanics, vol. 10, No. 8, pp. 401-406, 1995.

(Continued)

*Primary Examiner* — Nicholas Plionis
(74) *Attorney, Agent, or Firm* — Mark T. Vogelbacker; Reed Smith LLP (57) ABSTRACT

The current request reports an external fixation device to stabilize bone fractures with adaptable configuration during different stages of surgery or during treatment, through the generation of six degrees of freedom among the bone fragments. The device comprises numerous press-connector means, numerous cylindrical bars, numerous osteosynthesis screws and optionally from one to several rigid rings and one or more extension elements that permit generating diverse stable configurations to treat bone fractures.

9 Claims, 7 Drawing Sheets

(56) References Cited

FOREIGN PATENT DOCUMENTS

WO 03105704 12/2003
WO 2004026103 4/2004
WO WO 2010015813 A1 * 2/2010 ......... A61B 17/6466

OTHER PUBLICATIONS

Duda, et al., "A method to determine the 3-D stiffness of fracture fixation devices and its application to predict inter fragmentary movement." Journal of Biomechanics 31 (1998) 247-252.

Garcia, et al., "A nonlinear biphasic viscohyperelastic model for articular cartilage." Journal of Biomechanics 39 (2006) 2991-2998.
Gardner, et al., "Rapid application fracture fixators—an evaluation of mechanical performance." Clinic Biomechanics 16 (2001) 151-159.
Krischak, et al., "Effects of one-plane and two-plane external fixation on sheep osteotomy healing and complications." Clinic Biomechanics 17 (2002) 470-476.
Wilson, et al., "A fibril-reinforced poroviscoelastic swelling model for articular cartilage." Journal of Biomechanics 38 (2005) 1195-1204.

* cited by examiner

EXTERNAL FIXATION DEVICE ADAPTABLE FOR BONE FRACTURES

RELATED APPLICATIONS

This application is the United States National Stage of International Application No. PCT/IB2010/054571 filed Oct. 9, 2010, which was published as International Publication No. WO 2012/046109 A1. This application is incorporated by reference in its entirety herewith.

FIELD OF THE INVENTION

The invention relates to a medical device used in treating pathologies of the skeletal system, especially referring to an external fixation device to treat bone fractures.

BACKGROUND OF THE INVENTION

One of the important areas of biomechanics studies the mechanical behavior of biological tissue and orthopedic elements to determine the etiology of diseases and the development of medical devices used for the treatment of different pathologies of the musculo-skeletal system (J. J. Garcia, D. H. Cortés. A nonlinear biphasic viscohyperelastic model for articular cartilage. Journal of Biomechanics 39, pages 2991-2998, 2006; W. Wilson, C. C. van Donkelaar, B. van Rietbergen, R. Huiskes. A fibril-reinforced poroviscoelastic swelling model for articular cartilage. Journal of Biomechanics 38, pages 1195-1204, 2005). Among these elements, we find external fixation devices, indispensable tools for treating bone fractures. There are several configurations of external fixation devices, among which we may cite the unilateral configuration, the ring configuration, and the combined configuration, which gives rise to the hybrid fixation device. Configuration versatility, stability, and rigidity are among the essential features of a good external fixation device. These permit adequate reduction of the fracture and the formation of a good osseous callus after installation (Georg N. Duda, Helmut Kirchner, Hans-Joachim Wilke, Lutz Claes. A method to determine the 3-D stiffness of fracture fixation devices and its application to predict inter-fragmentary movement. Journal of Biomechanics 31, pages 247-252, 1998). It is also desirable for the fixation device to not be too bulky or heavy.

One of the models used widely is the Sardi fixation device, comprising presses (elements connecting the screws that penetrate the bone fragments to one or more bars) that permit four degrees of freedom between nails and connecting bars; its double-bar configuration provides very good stability and rigidity to the ensemble but it is very difficult to install when seeking to adequately reduce the fracture, given that it only permits two degrees of freedom among the fragments. Moreover, there are the double-bar unilateral configurations, assembled with connecting presses with five degrees of freedom, like those generally offered commercially, which limit the possibility of correcting deformities, given that it is not possible to vary the distance between the axles of the connecting cylindrical elements. A poorly aligned fracture may cause complications in neighboring articulations due to degenerative articular disease, secondary to abnormal pressure on the articular cartilage (V L Caja, W Kim, S Larsson, EYS Chao. Comparison of the machanical performance of three types of external fixators: linear, circular and hybrid. Clinical Biomechanics. Vol. 10, Issue 8, Pages 401-406, 1995.).

The resistance and stability of the external fixation system are critical factors (Gardner T N, Simpson H, Kenwright J. Rapid application fracture fixators—an evaluation of mechanical performance. Clinical Biomechanics. 16(2): 151-9, 2001). From this point of view, a double-bar system provides significantly greater stability than the single-bar system in which the slippage of a single connector implies the failure of the ensemble. Additionally, some studies have shown the influence of the rigidity of the fixation device on fracture healing (Gert D. Krischak, Andreas Janousek, Steffen Wolf, Peter Augat, Lothar Kinzl, Lutz E. Claes. Effects of one-plane and two-plane external fixation on sheep osteotomy healing and complications. Clinical Biomechanics 17, pages 470-476, 2002). For example, in experiments with animals it has been concluded axial inter-fragmentary displacements between 0.2-1 mm are optimal for fracture healing (Georg N. Duda, Helmut Kirchner, Hans-Joachim Wilke, Lutz Claes. A method to determine the 3-D stiffness of fracture fixation devices and its application to predict inter-fragmentary movement. Journal of Biomechanics 31, pages 247-252, 1998.).

In the patent literature, there are several devices for fracture fixation. For example, document WO2004/026103 describes a unilateral external fixation device that permits manipulation and fine adjustment of deformities by six degrees of freedom. The device is made up of an assembly bar and two moving joints, one on each side of the bar, each of which has two joints with a reduction gear mechanism with a concentric or axial helical mechanism and a locking mechanism to assure the device's degrees of freedom. The device is joined to the bone fragment through a press and one or more fastening screws.

Document WO1992/002184 presents an orthopedic manipulator for the reduction and stabilization of bone fractures through micrometric displacements by three degrees of freedom for both fragments and all the possible rotations via two sectors sliding one over the other reducing the opening angle; thus, permitting rotational and axial displacement of a portion of the bone.

Patent application WO1997/041790 describes an external fixation press adapted to fasten a locking screw to a connecting bar. The press includes a groove that transversely receives the connecting bar. A bolt is inserted through an opening transversely crossing said groove to join the connecting screw to the locking screw. Said connecting screw presents a surface attachment to the bar that fastens the connecting bar inside the groove increasing the press rigidity to prevent rotation around the bar and rotation of the connecting screw in the body of the press. Additionally, a device is described joining at least two connecting bars to guide the insertion of fastening screws between the bars. The device permits adjusting the distance between bars and presents different forms of union to the bars to facilitate installation of the press above or below the bars.

U.S. Pat. No. 6,428,540 introduces a device for repositioning fractured bone fragments comprising: a first press adapted to be joined to the bone by means of a first fastener; a second press adapted to be joined to the bone by means of a second fastener; three translational components associated to the presses that permit relative translational movement independent of the first press against the second press, along a first, second, and third translation axel where the three axels form an oblique-angle coordinated system; three rotation components associated to the presses permitting relative rotational movement independent of the first press against the second press, along a first, second, and third rotation axel; first and second parallel bars connecting the presses to the rotation and translation components, where the presses include a clamping jaw to receive the bone fasteners and a jaw that connects the clamping jaw to the parallel bars. The translation and rotation mechanisms permit altering the relative position of the presses in such a way that the device bears six degrees of freedom.

In spite of the different models existing commercially and in the literature, there is still a need for an external fixing device for bone trauma, which offers traumatologists greater versatility to adequately reduce the fracture; likewise, the configuration of the device must be adaptable during the different stages of surgery or during treatment through the incorporation of new elements or by eliminating others already assembled (screws, bars, presses, etc.).

The invention's external fixation device to stabilize bone introduces an adaptable configuration, which offers traumatology physicians greater versatility in placing nails and varying the distance between the axels of the cylindrical elements it connects—additional degree of freedom—, which permits adequately reducing the fracture, preserving the stability of the device through double-bar configurations. The versatility of the device permits modifying or adapting its configuration during the different stages of surgery or during treatment to allow, for example, including new elements (nails, bars, presses, etc.) or easily removing some already assembled elements without the need to completely disassemble the original configuration.

In the technical area, some of the advantages of the novel device from the present invention are: (1) It permits connecting a pair of screws from a bone fragment with a pair of screws from another bone fragment that are approximately on another plane, through a configuration of two bars and eight connecting presses. (2) Likewise, it permits connecting a pair of screws joined to the osseous diaphysis, located approximately on a plane, with another pair of screws from another fragment near the bone head, which are approximately on a transverse plane, perpendicular to the plane that approximately keeps the screws joined to the diaphysis, through a stable configuration of eight presses and three bars, without requiring other fastening elements. (3) Additionally, it permits connecting four or more osteosynthesis screws that are not perfectly aligned by using connecting presses and two bars. (4) It permits treating bone fractures to reduce the fracture without the need for the perfect alignment of the osteosynthesis screws joining the fastener to the bone fragments.

OBJECT OF THE INVENTION

In a first aspect, the invention offers an external fixation device to stabilize bone fractures comprising a plurality of press-connector media, a plurality of cylindrical bars, a plurality of osteosynthesis screws and optionally one or more rigid rings and one or more extension elements that permit generating diverse stable configurations for treating bone fractures.

DETAILED DESCRIPTION OF THE INVENTION

Figure 1:
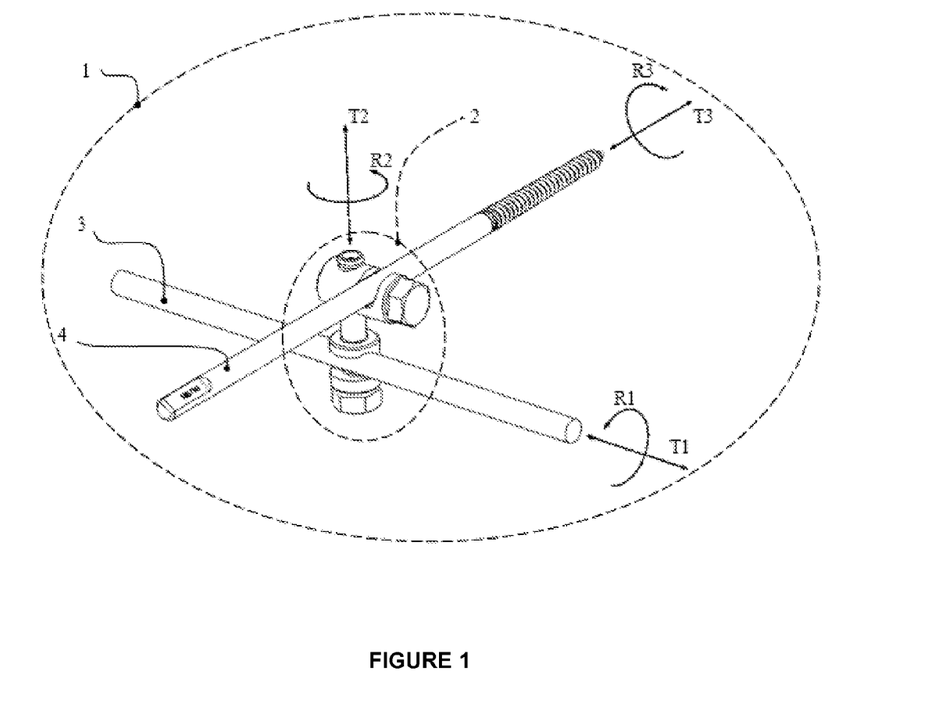
FIG. 1 presents a perspective of the external fixation device of the invention, showing the assembly of the press-connector, a cylindrical bar, and an osteosynthesis screw; possible translation movements (T1, T2, and T3) and rotation movements (R1, R2, and R3) between them are also shown.
Figure 6:
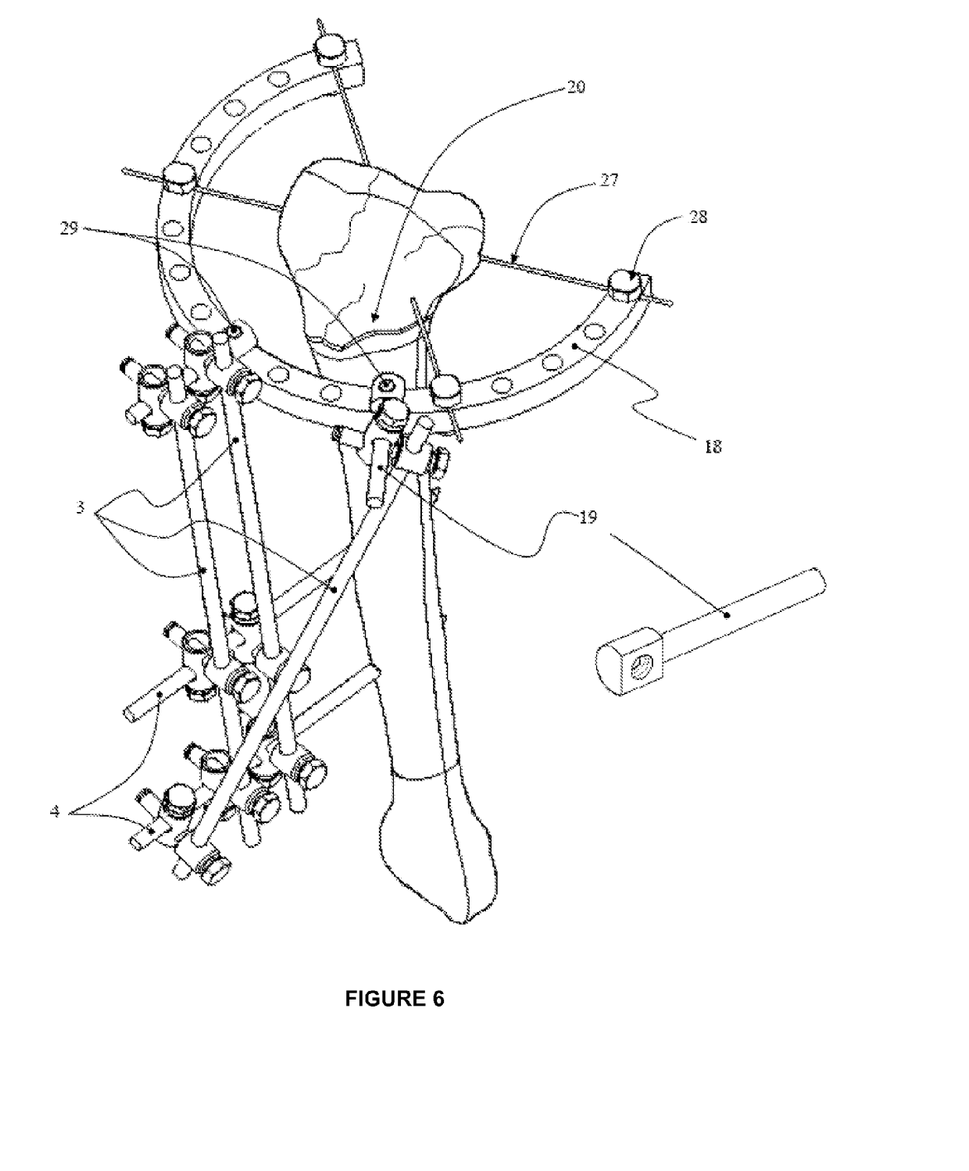
FIG. 6 presents a first hybrid configuration of the invention device for a fracture near the bone's upper epiphysis by adding a ring, two nails, and two additional presses.

FIG. 1 presents the invention's external fixation device (1) to stabilize bone fractures, which comprises a plurality of press-connector media (2), a plurality of cylindrical bars (3), a plurality of osteosynthesis screws (4) and optionally one or more rigid rings (18) and one or more extension elements (19) like those in FIG. 6, which permit generating diverse stable configurations to treat bone fractures.

Figure 2:
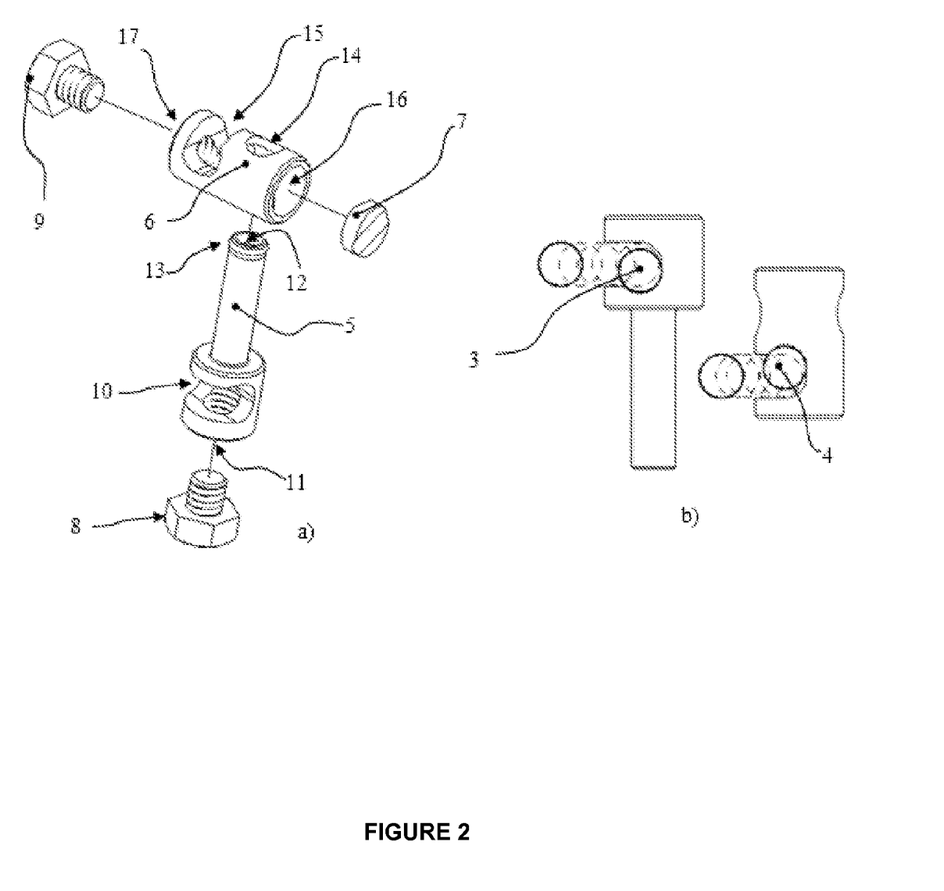
FIG. 2 shows the perspective of the configuration and disposition of the press-connector elements (a) and a lateral view of the disposition of the cylindrical elements in the invention's press-connector (b).

Regarding FIGS. 1 and 2, a press-connector element is described (2) of the external fixation device (1), which permits connecting two cylindrical elements in an infinite number of angular positions and orientations. The press-connector (2) is the fundamental element of this invention and it is made up of bodies (5) and (6) of approximately cylindrical shape, by an insertion element (7) and by two fastening screws (8) and (9).

Body (5) is a solid piece in tapering cylinder shape (two cylinders with different diameters joined amongst themselves). The end with the biggest diameter for body (5) has a slot (10) perpendicular to its axel, which has a cylindrical shape in the bottom to house a cylindrical element (3). Displacement T1 and rotation R1 of the cylindrical element (3) regarding body (5) are two of the degrees of freedom the press (2) permits activating or deactivating during its application. Activation or deactivation of these two degrees of freedom is controlled by adjusting a fastening screw (8) housed in a threaded perforation (11) whose axel coincides with that of the body (5) and which goes from the external flat surface of the cylinder with the biggest diameter to the intersection with the slot (10). When the screw is adjusted (8), its flat tip pushes the bar (3) against the slot's cylindrical surface (10) and, thus are fixed the two degrees of freedom existing between bodies (3) and (5). On the end with the smaller diameter for body (5) there is a tapered (cone-shaped) perforation (12) which is not very deep and whose axel coincides with that of the body (5). This perforation (12) plays an important role in keeping together the press-connector element components (2) for which the end diameter is expanded (13) in the cylinder with the smaller diameter by means of forced thrust from a tapered (cone-shaped) punch, making this end to fulfill the stop function.

The body shown (6) corresponds to a cylindrical piece that comprises a transversal perforation (14), a transversal slot (15) perpendicular to its axel, and two axial perforations (16) and (17). The transversal perforation (14) and the transversal slot (15) present the axel in diametrical direction and completely cross the cylindrical body (6). The axels for perforations (16) and (17) coincide with the axel for the body (6). The axial perforation (16) of greater diameter goes from one of the flat surfaces of the body (6) to the complete intersection with the perforation (14) and the transversal slot (15). The other axial perforation (17) of smaller diameter goes from the other flat surface of the body (6) to the complete intersection with the slot (15). This perforation (17) is threaded along its whole length to house a fastening screw (9).

The insertion element (7), with an approximately cylindrical shape, is formed from a solid cylinder on whose flat surfaces two semi-cylindrical surfaces have been machined with their axels perpendicular to the axel of the element (5) and perpendicular amongst themselves. The external diameter of the insertion element (7) is such that it can slide into the axial perforation (16) of the body (6).

The body (6) functions in conjunction with the insertion element (7), the body (5) and a fastening screw (9). First, the cylinder of the body (5) slides (thrusts) and rotates in the cylindrical perforation (14) of the body (6), in such a manner that this thrust, T2, and rotation, R2, when transmitted to the bar (3) constitute another two degrees of freedom for the press-connector (2), which together with the two previously mentioned complete four degrees of freedom until now. Furthermore, the insertion element (7) slides into the body (6) perforation (16). In the body (6) slot (15) the osteosynthesis screw (4) of cylindrical configuration thrusts and rotates, in such a way that the thrust, T3, and rotation, R3, of this element in the slot (15) constitute the other two degrees of freedom of the press (2); thus, completing a total of six degrees of freedom (T1, T2, T3, R1, R2, and R3) among the elements connected by the press-connector (2). To fix the four degrees of freedom (T2, R2, T3, and R3) related to the body (6), regulate the adjustment screw (9) that slides in the perforation thread (17). The flat end of this screw makes contact against the osteosynthesis screw (4), which pushes the insertion element (7), while this one pushes the smaller cylindrical portion of the body (5), which leans against the body (6) perforation cavities (14).

According to what has been described, two of the press-connector (2) degrees of freedom in this invention are associated to body (5) and the other four are associated to body (6). To fix the degrees of freedom (T1 and R1) associated with body (5) regulate the adjustment screw (8) and to set the degrees of freedom (T2, R2, T3, and R3) associated with body (6) fix the fastening screw (9). Unlike any other state-of-the-art press, the press-connector (2) permits the variability of the distance between the axels of the bars being connected. Also, as shown in FIG. 2b, this press-connector (2) permits the introduction of elements to be connected in two different ways: the first alternative consists of introducing the cylindrical elements to be connected (3) or (4) inserting them axially through the end of the slots (10) or (15) as it corresponds, while a second alternative consists of inserting the cylindrical elements to be connected (3) or (4) through a transversal movement of these to the cylindrical surface of corresponding slot.

Likewise, when the device of the invention is applied, for example, to a fracture near the upper epiphysis of the bone (20), in addition to the press-connector (2) and the cylindrical elements to be connected (3) or (4), a rigid ring (18) is optionally incorporated with perforations and an extension element (19) that permits joining the rigid ring (18) with the cylindrical elements to be connected (3) or (4). In this configuration, the bone head fragments are joined with wires, which are fixed to the rigid ring (18) via screws with holes. Then, the rigid ring (18) is joined to the extension elements (19) via fastening screws, which are in turn joined through bars (3) to nails connected to the bone diaphysis.

These characteristics permit the configurations constructed with this fixation device to be very versatile, simple, and stable, given that they can be accomplished with the combination of very few elements. Furthermore, from the mechanical point of view, the device offers a transmission of direct forces between pins or screws anchored to the bone fragments.

From these elements previously described, the traumatologist physician can assemble a device according to the specific requirements of the fracture; hence, the following examples are merely illustrative with respect to the possibilities of the device assembly and do not seek in any way to limit the probable configurations of the device itself.

Example 1

Assembly of the Device Applied to a Fracture Near The Epiphysis or Tibial Head

Figure 3:
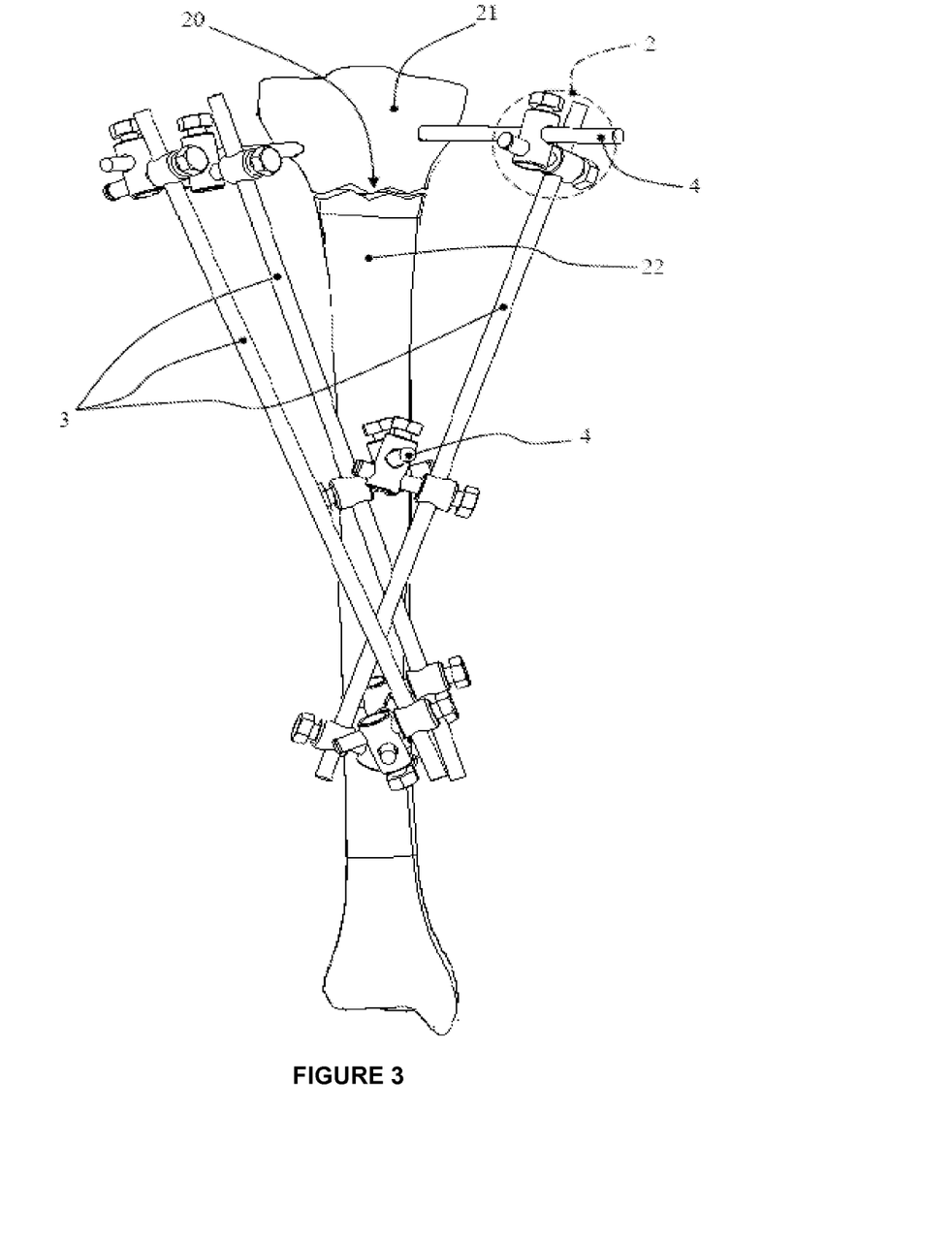
FIG. 3 presents the invention device configuration for a fracture near the tibial epiphysis.

In the configuration of the invention device for a fracture (20) near the tibial epiphysis or head (21) (FIG. 3) set two screws that penetrate bone diaphysis (22) with another two screws anchored to the bone head and which are approximately comprised on a transversal plane approximately perpendicular to the plane, which approximately comprises the screws anchored on the diaphysis. It is important to highlight that there is absolute freedom to locate each of the screws and that the device functions without the need for pairs of screws to be comprised exactly on a plane. It should be noted that, unlike other systems, this assembly can be constructed with the use of only three parts: the connecting press (2), the bars (3), and the osteosynthesis screws (4). In this assembly, one of the screws (4) from the bone head is joined to the other two diaphysis screws (4) through a bar (3) and three connecting presses (2). The bar passes between the diaphysis screws (4) and the use of the connecting presses (2) with six degrees of freedom, permits the direct connection to each screw (4) without the necessity for using other elements, like it is done by other fixation systems. Another bar (3) connects the additional screw (4) from the bone head to the two screws (4) on the diaphysis through three connecting presses (2). Finally, and for the purpose of guaranteeing perfect stability of the device, an additional bar connects one of the screws (4) in the diaphysis to one of the screws (4) from the head through two presses (2). This configuration is perfectly stable and allows the orthopedic physician six degrees of freedom between the bone fragments.

Example 2

Assembly of the Device for a Tibial Diaphyseal Fracture

Figure 4:
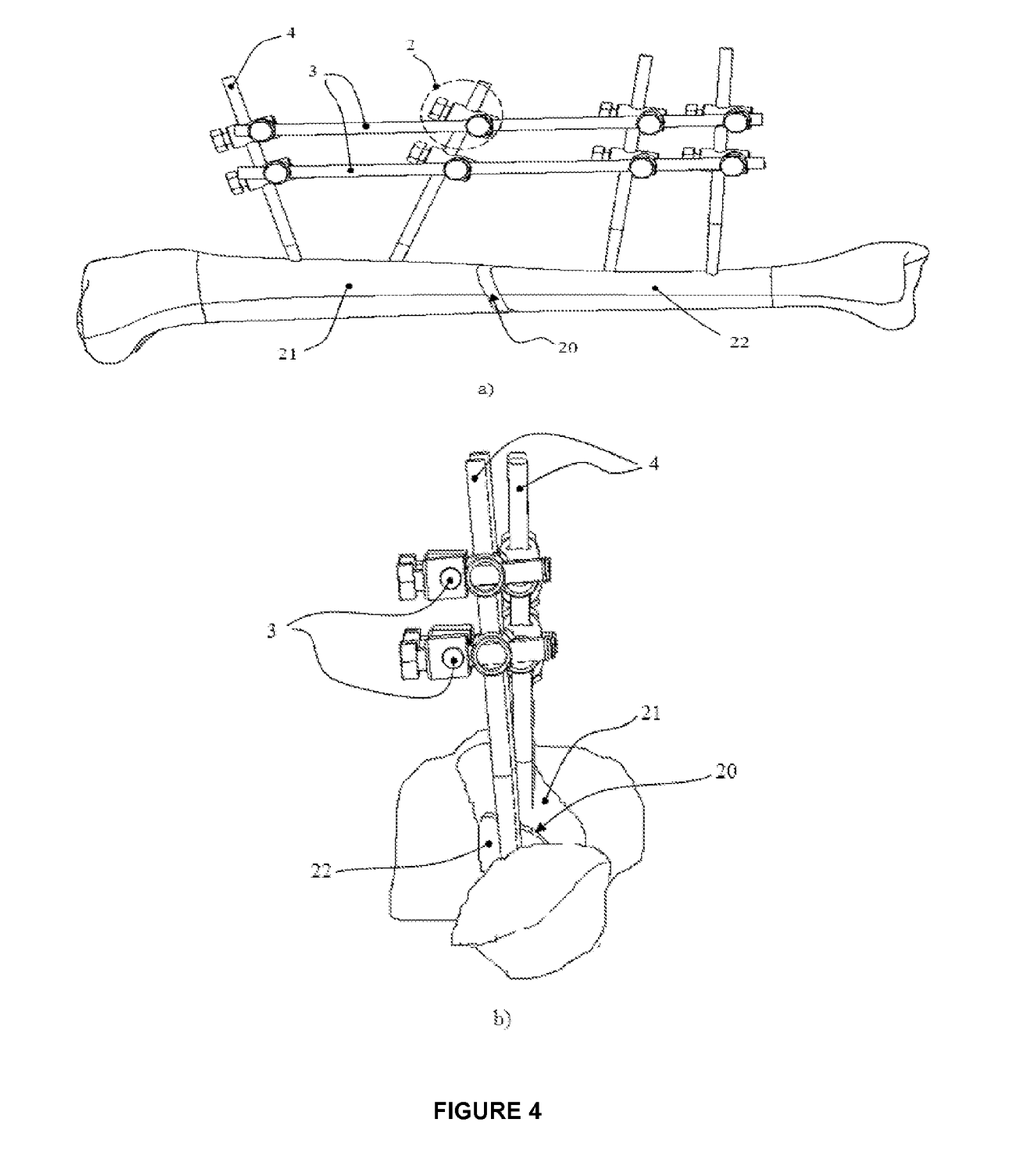
FIG. 4 presents the invention device configuration for a fracture of the tibial diaphysis seen from the side (a) and from distal end (b).

In this assembly (FIG. 4), two nails from the bone fragment (21) are fixed to two nails from the fragment (22) through two bars (3) and eight connecting presses (2). It should be noted that there is an infinite number of positions and orientations for the screws (4) and that unlike other systems using presses with five degrees of freedom and requiring for the screws (4) to remain on a same plane, the device in this invention permits the screws (4) to be on different planes with different angular deviations.

Example 3

Figure 5:
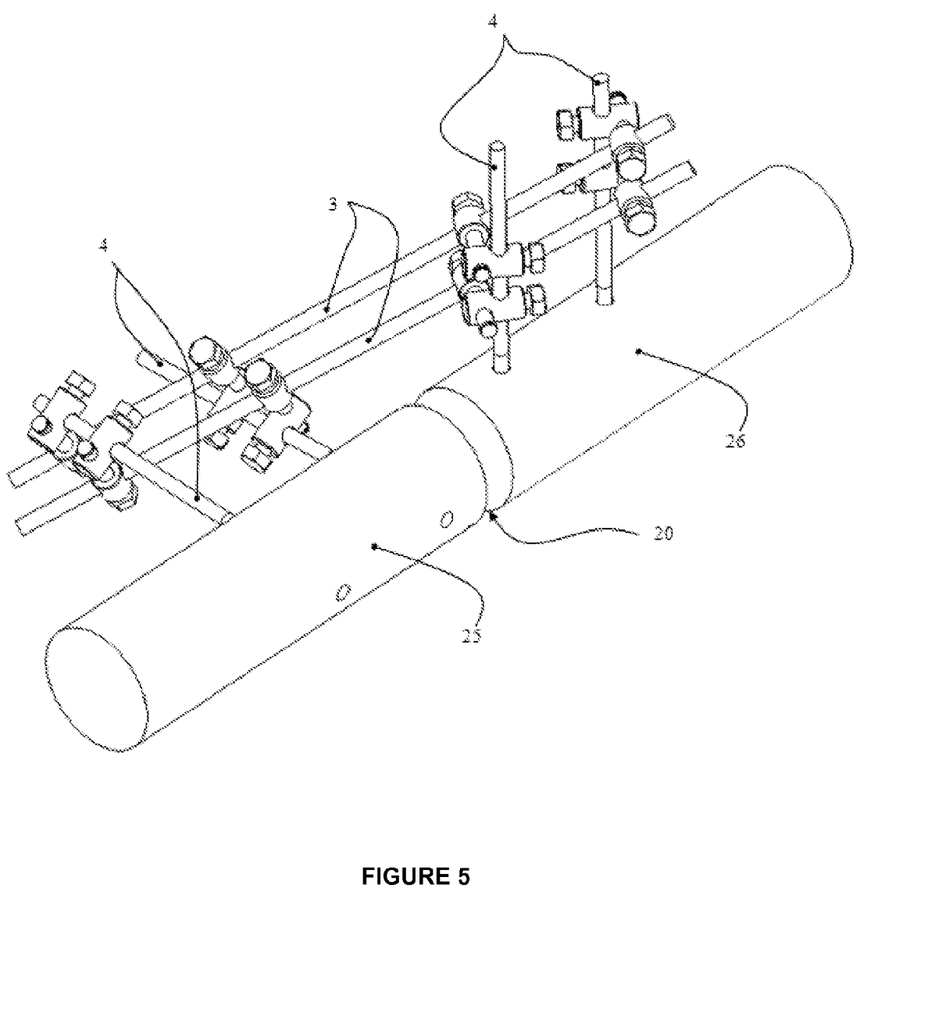
FIG. 5 presents the invention device configuration for a fracture of the tibial diaphysis with the nails from each fragment on different planes.

Assembly of the Device Applied to a Diaphyseal Fracture with Two Nails in Fragments Forming Different Planes En la Figura 5 se muestran los fragmentos de hueso representados por cilindros. En este ensamble se fijan dos tornillos (4) unidos a uno de los fragmentos (25) con dos clavos unidos al otro fragmento (26). Los dos pares de tornillos de cada fragmento aproximadamente pertenecen a dos pianos que forman entre ellos un ángulo aproximadamente perpendicular, es decir, que existe libertad para fijar la posición y orientación de cada tornillo. En este ensamble las barras (3) pasan por el espacio entre tornillos de cada fragmento, lo cual solo es posible mediante la utilización de las prensas connectoras (2) de seis grados de libertad de la presente invención. Este ensamble permite activar todos los grados de libertad entre los fragmentos de hueso para reducir adecuadamente la fractura y brindar una excelente estabilidad al dispositivo con su configuración de doble barra.

Example 4

Figure 7:
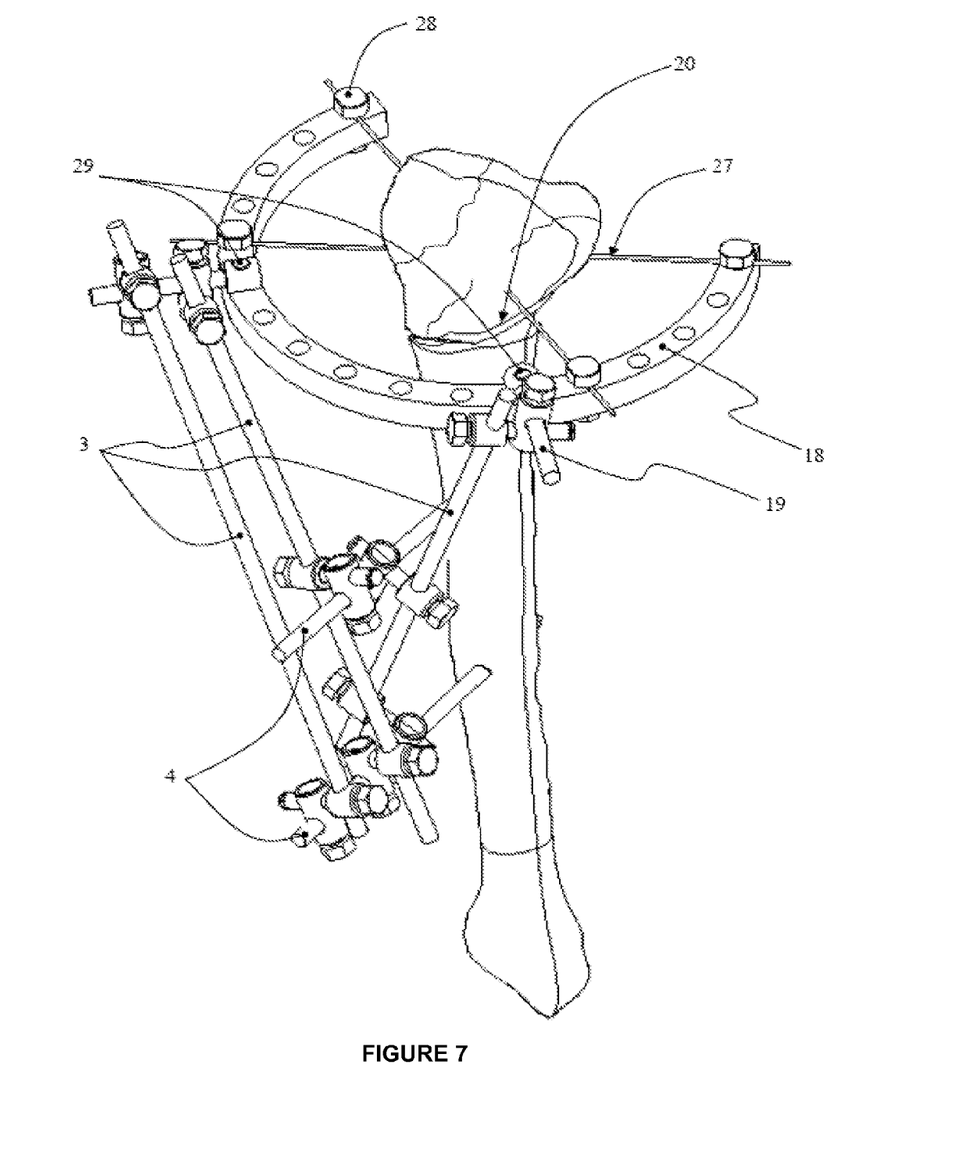
FIG. 7 presents a second hybrid configuration of the invention device for a fracture near the bone's upper epiphysis.

Assembly of the Device in Hybrid Form Applied to a Fracture Near the Epiphysis or Tibial Head FIG. 6 shows the application of the invention device on a comminuted fracture in the zone of the bone's upper epiphysis, which is known as tibial plateau fracture. This assembly, in addition to the connecting press (2) and the bars (3), uses a rigid ring (18) with perforations, an extension element (19) that permits joining the ring (18) to the bars, osteosynthesis wires (27), and the wire-adjustment screws (28). In this assembly, the bone head fragments are joined with two crossing wires (27), each of which is fixed to the ring (18) through screws with passing holes (28). Two extension elements (19) are fixed to the ring (18) through a headed adjustment screw (29) applied from the ring's lower side. This is accomplished by making the adjustment screw (29) to cross any of the flat perforations of the ring (18) and screwing it in the threaded perforation of the extension element (19). Then, three bars are mounted (3) connecting with the extension elements (19) and with the osteosynthesis screws (4) adjusting each pair of elements through connecting presses (2). In the configuration already described, two of the three bars (3) pass in approximately parallel manner on one side of the diaphysis screws (4); however, these could pass through the space between the diaphysis screws (4), as shown in the assembly on FIG. 7, which is only possible by using the connecting presses (2) of six degrees of freedom from this invention. The purpose of the third bar (3) is to ensure the stability of the device and increase rigidity on all the planes.

Although this invention has been described through non-limiting preferred embodiments shown of the invention, it remains understood that the modifications and variations that preserve its essential and elemental contents are understood in the scope of the attached claims.

The invention claimed is:

1. An external fixation device to stabilize bone fractures comprising:
   a plurality of press-connector media, each press-connector media comprising a first body and a second body, each of said first body and said second body having a cylindrical shape, said first body including a first cylindrical structure and a second cylindrical structure, the second cylindrical structure including a conical perforation having a diameter and an axis that coincides with an axis of said first body, the conical perforation located at an end of the second cylindrical structure opposite to the first cylindrical structure, the first cylindrical structure including a slot extending perpendicularly to the axis of the first body and a threaded perforation having an axis the coincides with the axis of the first body, the threaded perforation intersecting with the slot, the second body including a transversal slot, a first axial perforation at one end of the second body and a second axial perforation at an opposing end of the second body;
   each of said plurality of press-connector media further comprising an insertion element having a cylindrical shape, a first clamping screw and a second clamping screw, the insertion element being configured to be inserted into the first axial perforation of the second body, the first clamping screw being configured to be inserted into the threaded perforation of the first cylindrical structure of the first body, the second clamping screw being configured to be inserted into the second axial perforation of the second body;
   one or more cylindrical bars; and
   one or more osteosynthesis screws, at least a portion of one of the one or more osteosynthesis screws being received in the transversal slot of the second body.

2. The external fixation device to stabilize bone fractures of claim 1, wherein said plurality of press-connector media permits connecting said first body and said second body in a plurality of angular positions and orientations.

3. The external fixation device to stabilize bone fractures of claim 1 or 2, wherein said first cylindrical structure of said first body has a first diameter and said second cylindrical structure of said first body has a second diameter smaller than said first diameter.

4. The external fixation device to stabilize bone fractures of claim 1, wherein said first axial perforation has a first diameter and the second axial perforation has a second diameter, the second diameter being smaller than the first diameter, axes of the first and second axial perforations coincide with the axis of said second body; wherein said second axial perforation includes a threading element throughout its length to accommodate said second clamping screw.

5. The external fixation device to stabilize bone fractures of claim 4, wherein said insertion element has a smaller diameter than the first diameter of said first axial perforation so that said insertion element can glide on said second body.

6. The external fixation device to stabilize bone fractures of claim 1, wherein said plurality of press-connector media has six degrees of freedom and wherein two of said six degrees of freedom are associated with said first body and four remaining of said six degrees of freedom are associated with said second body and wherein said six degrees of freedom are fixed with the first clamping screw and with the second clamping screw.

7. The external fixation device to stabilize bone fractures of claim 1, wherein said plurality of press-connector media permit a distance between the axes of the first and second bodies to be variable.

8. The external fixation device to stabilize bone fractures of claim 1, wherein an extension element joins a rigid ring with said first and second bodies and wherein said rigid ring is joined to said extension element through said first and second clamping screws, which in turn are joined through said one or more bars to said one or more osteosynthesis screws.

9. The external fixation device to stabilize bone fractures of claim 1, wherein said press-connector media permit six degrees of freedom.

\* \* \* \* \*